US009974868B2

(12) United States Patent
Gao et al.

(10) Patent No.: US 9,974,868 B2
(45) Date of Patent: May 22, 2018

(54) OCTAPOD IRON OXIDE NANOPARTICLES AS HIGH PERFORMANCE $T_2$ CONTRAST AGENTS FOR MAGNETIC RESONANCE IMAGING

(71) Applicants: The United States of America, as represented by the Secretary, Department of Health and Human Services, Washington, DC (US); Xiamen University, Xiamen, Fujian (CN)

(72) Inventors: Jinhao Gao, Fujian (CN); Xiaoyuan Chen, Potomac, MD (US); Zenghuan Zhao, Chongqing (CN)

(73) Assignees: The United States of America, as represented by the Secretary, Department of Health and Human Services, Washington, DC (US); Xiamen University, Xiamen (CN)

( * ) Notice: Subject to any disclaimer, the term of this patent is extended or adjusted under 35 U.S.C. 154(b) by 0 days. days.

(21) Appl. No.: 14/895,745

(22) PCT Filed: Jun. 3, 2013

(86) PCT No.: PCT/CN2013/076645
§ 371 (c)(1),
(2) Date: Dec. 3, 2015

(87) PCT Pub. No.: WO2014/194458
PCT Pub. Date: Dec. 11, 2014

(65) Prior Publication Data
US 2016/0129138 A1      May 12, 2016

(51) Int. Cl.
*A61K 49/18*        (2006.01)
*A61K 49/06*        (2006.01)
*C01G 49/08*        (2006.01)
*A61K 49/08*        (2006.01)

(52) U.S. Cl.
CPC .......... *A61K 49/1833* (2013.01); *A61K 49/06* (2013.01); *A61K 49/08* (2013.01); *A61K 49/1818* (2013.01); *A61K 49/1851* (2013.01); *C01G 49/08* (2013.01)

(58) Field of Classification Search
None
See application file for complete search history.

(56) References Cited

U.S. PATENT DOCUMENTS

| 6,232,264 | B1 | 5/2001 | Lukehart et al. |
| 6,627,556 | B1 | 9/2003 | Aronowitz et al. |
| 2009/0208580 | A1* | 8/2009 | Shi ............. A61K 9/5146 424/489 |
| 2010/0317503 | A1 | 12/2010 | Subramanian et al. |
| 2011/0286938 | A1* | 11/2011 | Thurman ........... A61K 49/1812 424/9.323 |

FOREIGN PATENT DOCUMENTS

| CN | 101011587 A | 8/2007 |
| CN | 102896312 A | 1/2013 |
| WO | WO 2007/021621 A2 | 2/2007 |
| WO | WO 2011/138975 A1 | 11/2011 |
| WO | WO 2012/001578 A1 | 1/2012 |

OTHER PUBLICATIONS

Bronstein, L.M., et al., "Nanoparticles by Decomposition of Long Chain Iron Carboxylates: From Spheres to Stars and Cubes", Langmuir, 2011, pp. 3044-3050.*
Matijevic, E., et al. "Production of Monodispersed Colloidal Particles", Ann. Rev. Mater. Sci., 1985, pp. 483-516.*
Davis, J.A., et al., "Effect of Adsorbed Complexing Ligands on Trace Metal Uptake by Hydrous Oxides", Env. Eng. Sci., 1978, pp. 1309-1315.*
Hou, Y., et al., "Controlled Synthesis and Chemical Conversions of FeO Nanoparticles", Agnew. Chem. Intt., 2007, pp. 6329-6332.*
Khurshid, H., et al., "Synthesis and magnetic properties of core/shell FeO/Fe3O4 nano-octopods", J. Appl. Phys., 2013, pp. 1-3.*
Zhou, Z., et al., "A Synergistically Enhanced T1-T2 Dual-Modal Contrast Agent", Adv. Mater., 2012, pp. 6223-6228.*
Ardizzone, S., et al., "Interactions of CL—ions with Fe3O4", 1983, J. Electroanal. Chem., pp. 301-305.*
Ananta et al., "Geometrical confinement of gadolinium-based contrast agents in nanoporous particles enhances T1 contrast," *Nat Nanotechnol.*, 5 (11), 815-821 (2010) author manuscript.
Bulte et al., "Iron oxide MR contrast agents for molecular and cellular imaging," *NMR Biomed.*, 17 (7), 484-499 (2004).
Corot et al., "Recent advances in iron oxide nanocrystal technology for medical imaging," *Adv. Drug Deliv. Rev.*, 58 (14), 1471-1504 (2006).
Gao et al., "Multifunctional magnetic nanoparticles: design, synthesis, and biomedical applications," *Acc. Chem. Res.*, 42 (8), 1097-1107 (2009).
Ghosh et al.,"M13-templated magnetic nanoparticles for targeted in vivo imaging of prostate cancer," *Nat Nanotechnol.*, 7 (10), 677-682 (2012) author manuscript.
Harisinghani et al., "Noninvasive detection of clinically occult lymph-node metastases in prostate cancer," *N. Engl. J. Med.*, 348 (25), 2491-2499 (2003).
Huang et al., "Amine-Assisted Synthesis of Concave Polyhedral Platinum Nanocrystals Having {411} High-Index Facets," *J. Am. Chem. Soc.*, 133 (13), 4718-4721 (2011).
International Preliminary Report on Patentability, Application No. PCT/CN2013/076645, dated Dec. 8, 2015.
International Search Report, Application No. PCT/CN2013/076645, dated Mar. 14, 2014.
Kim et al., "Large-scale synthesis of uniform and extremely small-sized iron oxide nanoparticles for high-resolution T1 magnetic resonance imaging contrast agents," *J. Am. Chem. Soc.*, 133 (32), 12624-12631 (2011).

(Continued)

*Primary Examiner* — Michael G Hartley
*Assistant Examiner* — Lance W Rider
(74) *Attorney, Agent, or Firm* — Leydig, Voit & Mayer, Ltd.

(57) ABSTRACT

Disclosed are nanoparticles comprising octapod iron oxide having eight trigonal bipyramidal arms and a method of preparing the same. The nanoparticles are prepared by heating a mixture of a ferric carboxylate, a carboxylic acid, a chloride salt, water, and a non-polar solvent, to a temperature above about 300° C. Also disclosed is a method of magnetic resonance imaging a tissue in a mammal, comprising use of the aforesaid nanoparticles.

14 Claims, 13 Drawing Sheets

(56) References Cited

OTHER PUBLICATIONS

Laurent et al., "Magnetic Iron Oxide Nanoparticles: Synthesis, Stabilization, Vectorization, Physicochemical Characterizations, and Biological Applications," *Chem. Rev.*, 108 (6), 2064-2110 (2008).

Lee et al., "Designed synthesis of uniformly sized iron oxide nanoparticles for efficient magnetic resonance imaging contrast agents," *Chem. Soc. Rev.*, 41 (7), 2575-2589 (2012).

Lee et al., "Magnetosome-like ferrimagnetic iron oxide nanocubes for highly sensitive MRI of single cells and transplanted pancreatic islets," *Proc. Natl. Acad. Sci. USA.*, 108 (7), 2662-2667 (2011).

Major et al., "Bioresponsive, cell-penetrating, and multimeric MR contrast agent," *Acc. Chem. Res.*, 42 (7), 893-903 (2009) author manuscript.

Park et al., "Ultra-large-scale syntheses of monodisperse nanocrystals," *Nat. Mater.*, 3 (12), 891-895 (2004).

Tassa et al., "Dextran-coated iron oxide nanoparticles: a versatile platform for targeted molecular imaging, molecular diagnostics, and therapy," *Acc. Chem. Res.*, 44 (10), 842-852 (2011) author manuscript.

Terreno et al., "Challenges for molecular magnetic resonance imaging," *Chem. Rev.*, 110 (5), 3019-3042 (2010).

Weissleder et al., "Ultrasmall superparamagnetic iron oxide: characterization of a new class of contrast agents for MR imaging," *Radiology*, 175 (2), 489-493 (1990).

Written Opinion of the International Searching Authority, Application No. PCT/CN2013/076645, dated Mar. 3, 2014.

Zabow et al., "The fabrication of uniform cylidrical nanoshells and their use as spectrally tunable MRI contrast agents," *Nanotechnology*, 20 (38), 385301 (2009).

Zhang et al., "Synthesis of Pd—Pt bimetallic nanocrystals with a concave structure through a bromide-induced galvanic replacement reaction," *J. Am. Chem. Soc.*, 133 (15), 6078-6089 (2011).

Zhang et al., "Concave cubic gold nanocrystals with high-index facets," *J. Am. Chem. Soc.*, 132 (40), 14012-14014 (2010).

Zhang et al., $Cu^{2+}$-assisted synthesis of hexoctahedral Au—Pd alloy nanocrystals with high-index facets, *J. Am. Chem. Soc.*, 133 (43), 17114-17117 (2011).

Zhou et al., "A synergistically enhanced T(1)-T(2) dual-modal contrast agent," *Adv. Mater.*, 24 (46), 6223-6228 (2012) author manuscript.

De Montferrand et al., "Iron oxide nanoparticles with sizes, shapes and compositions resulting in different magnetization signatures as potential labels for multiparametric detection," *ACTA Biomaterialia*, 9(4): 6150-6157 (2013).

Perez, Manuel J., "Iron oxide nanoparticles: Hidden Talent," *Nature Nanotechnology*, 2(9): 535-536 (2007).

Zhao et al., "Octapod iron oxide nanoparticles as high-performance T2 contrast agents for magnetic resonance imaging," *Nature Communications*, 4: 7 pages. (2013).

\* cited by examiner

OCTAPOD IRON OXIDE NANOPARTICLES AS HIGH PERFORMANCE T$_2$ CONTRAST AGENTS FOR MAGNETIC RESONANCE IMAGING

CROSS-REFERENCE TO A RELATED APPLICATION

This patent application is the U.S. national phase of International Patent Application No. PCT/CN2013/076645, filed Jun. 3, 2013, which is incorporated by reference.

BACKGROUND OF THE INVENTION

Magnetic resonance imaging (MRI) plays a critically important role in molecular imaging and clinical diagnosis because it is non-invasive and capable of producing images with high spatial and temporal resolution (Laurent, S. et al., *Chem. Rev.* 108, 2064-2110 (2008); Tassa, C. et al., *Acc. Chem. Res.* 44, 842-852 (2011); Corot, C. et al., *Adv. Drug Deliv. Rev.* 58, 1471-1504 (2006)). Approximately 35% of clinical MR scans need contrast agents to improve the sensitivity and diagnostic accuracy (Major, J. L. et al., *Acc. Chem. Res.* 42, 893-903 (2009)). For example, superparamagnetic iron oxide (SPIO) nanoparticles are the most common T$_2$ contrast agents, such as Feridex™ and Resovist™, especially for the imaging and detection of lesions from normal tissues (Weissleder, R. et al., *Radiology* 175, 489-493 (1990); Bulte, J. W. M. et al., *NMR Biomed.* 17, 484-499 (2004); Harisinghani, M. G. et al., *N. Engl. J. Med.* 348, 2491-2495 (2003); Gao, J. H. et al., *Acc. Chem. Res.* 42, 1097-1107 (2009)).

However, there are several deficiencies in the presently available T$_2$ contrast agents (e.g., Feridex™ and Resovist™) in clinical use. As they are intrinsically negative contrast agents, false positive diagnosis may be found in the hypointense areas such as blood pooling, calcification, and metal deposition (Terreno, E. et al., *Chem. Rev.* 110, 3019-3042 (2010); Kim, B. H. et al., *J. Am. Chem. Soc.* 133, 12624-12631 (2011); Lee, N. et al., *Chem. Soc. Rev.* 41, 2575-2589 (2012)). In particular, the commercially available T$_2$ contrast agents exhibit poor crystallinity and relatively low relaxivity (Lee, N. et al., *Proc. Natl. Acad. Sci. USA.* 108, 2662-2667 (2011)). Thus, a limitation of MRI at present is the relatively low sensitivity of the contrast agents (Ananta, J. S. et al., *Nat Nanotechnol.* 5, 815-821 (2010); Ghosh, D. et al., *Nat Nanotechnol.* 7, 677-682 (2012). Therefore, there exists an unmet need for new T$_2$ contrast agents with high relaxivity for enabling high-performance MRI.

BRIEF SUMMARY OF THE INVENTION

The foregoing need has been satisfied by the present invention.

The invention provides nanoparticles comprising octapod iron oxide having eight trigonal bipyramidal arms.

The invention also provides encapsulated nanoparticles comprising nanoparticles comprising octapod iron oxide having eight trigonal bipyramidal arms and an encapsulating agent.

The invention further provides a method of preparing nanoparticles comprising octapod iron oxide having eight trigonal bipyramidal arms, which method comprises heating a mixture of a ferric carboxylate, a carboxylic acid, a chloride salt, and a solvent.

The invention additionally provides a method of imaging a tissue in a mammal, comprising administering to the mammal nanoparticles comprising octapod iron oxide having eight trigonal bipyramidal arms, and obtaining a magnetic resonance image of the tissue.

The inventive nanoparticles comprising octapod iron oxide exhibit ultrahigh r$_2$ values. For example, nanoparticles comprising octapod iron oxide having an edge length of 30 nm exhibit an r$_2$ value of approximately 679.3±30 mM$^{-1}$ s$^{-1}$, which is approximately 5.4 times larger than that of spherical iron oxide nanoparticles with similar geometric volume. The ultrahigh r$_2$ values are probably due to the highly increased effective radius and strong local field inhomogeneity of the unique magnetic core. Compared to spherical iron oxide nanoparticles, these octapod iron oxide nanoparticles are much more effective T$_2$ contrast agents for in vivo MRI and small tumor detection, which holds great promise for highly sensitive, early stage and accurate detection of cancer in the clinic.

BRIEF DESCRIPTION OF THE SEVERAL VIEWS OF THE DRAWING(S)

Figure 4:
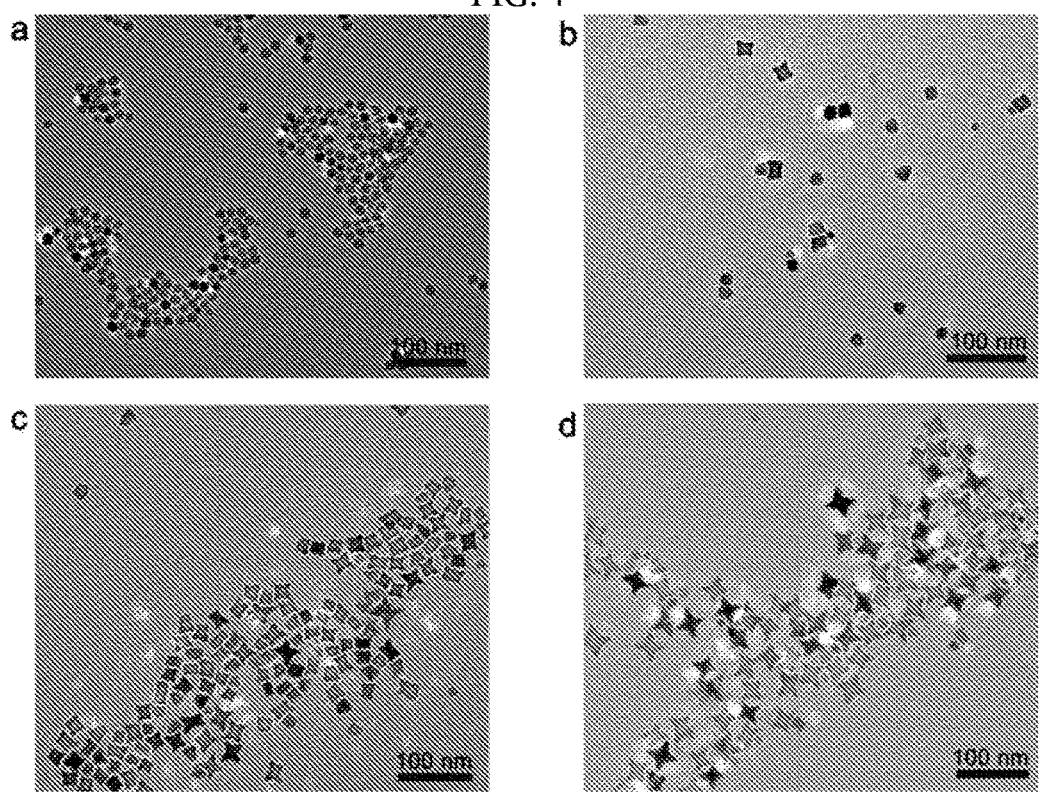

FIG. 4 depicts TEM images of iron oxide nanoparticles obtained by reacting 0.86 mmole of iron oleate with 0 mg (a), 2 mg (0.034 mmole) (b), 5 mg (0.085 mmole) (c), and 10 mg (0.17 mmole) (d) of sodium chloride, in accordance with an embodiment of the invention.

Figure 5:
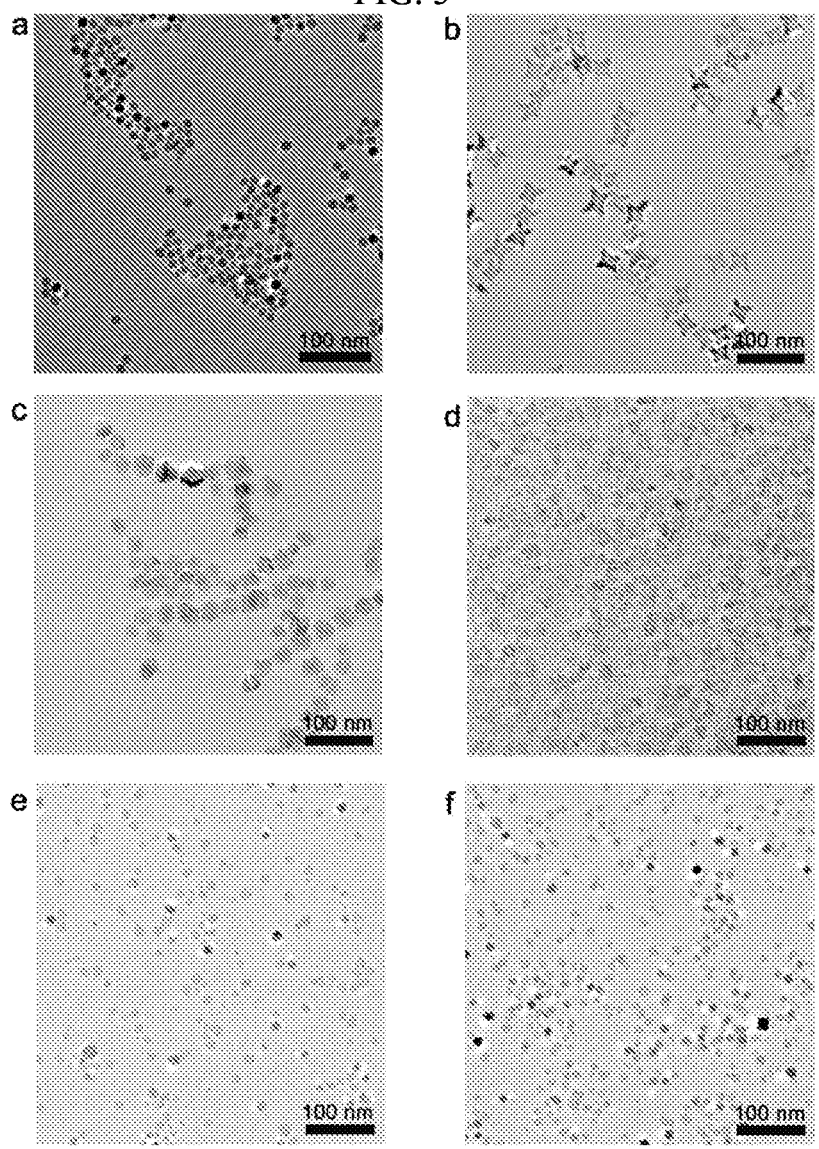

FIG. 5 depicts TEM images of iron oxide nanoparticles obtained by reacting iron oleate with (a) no salts, (b) NaCl, (c) KBr, (d) NaF, (e) sodium oleate, and (f) NaOH.

Figure 6:
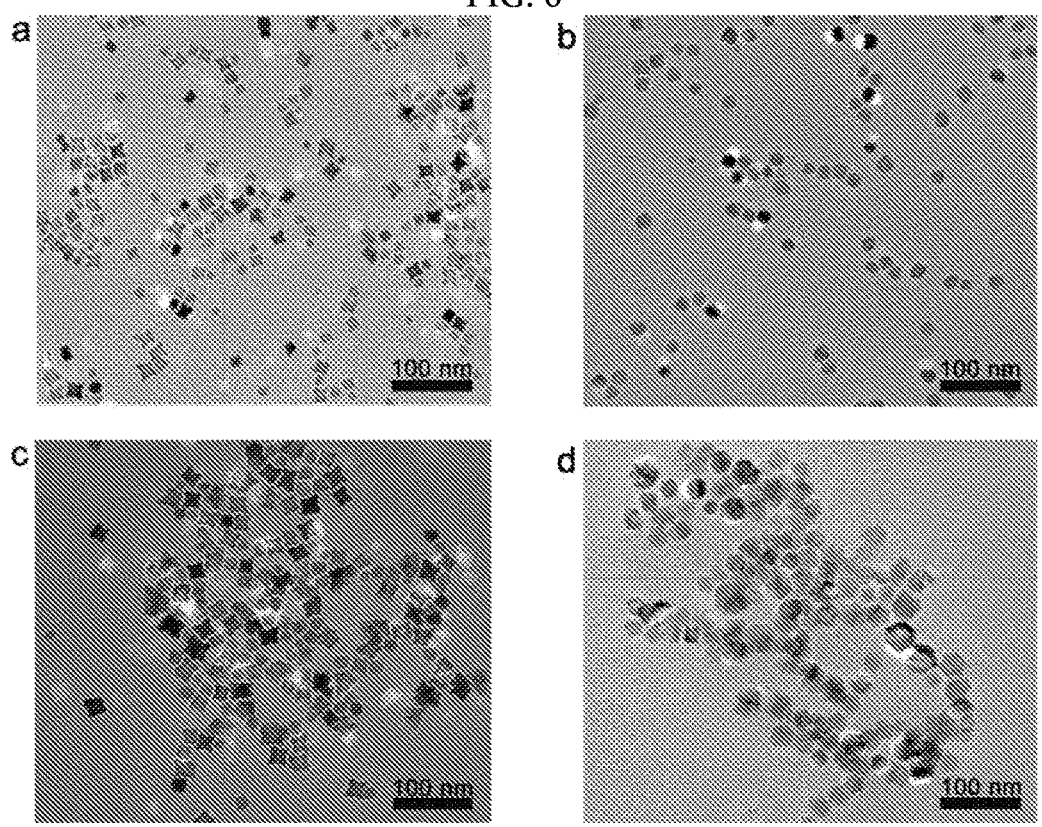

FIG. 6 depicts TEM images of iron oxide nanoparticles obtained by replacing sodium chloride with (a) hexadecyl trimethyl ammonium chloride, (b) hexadecyl trimethyl ammonium bromide, (c) KCl, and (d) KBr, in accordance with an embodiment of the invention.

Figure 7:
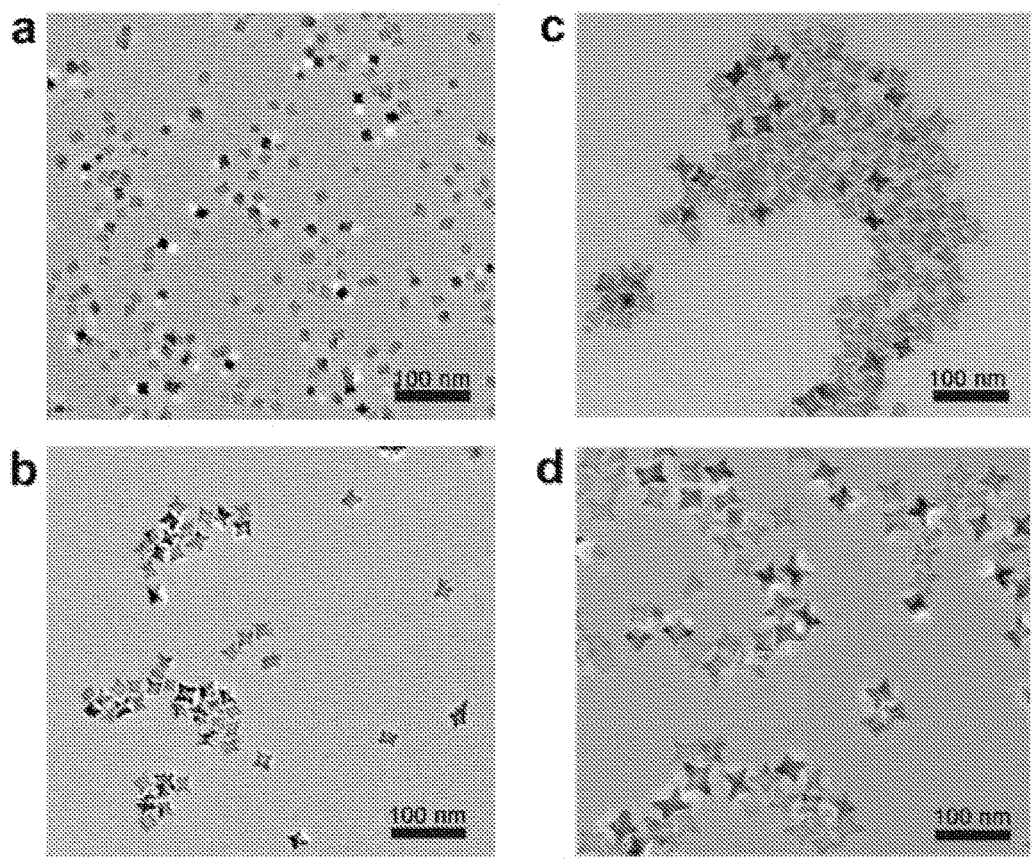

FIG. 7 depicts TEM images of iron oxide nanoparticles obtained by reacting iron oleate in the presence of sodium chloride for (a) 0.5 h, (b) 1 h, (c) 2 h, and (d) 2.5 h, in accordance with an embodiment of the invention.

Figure 8:
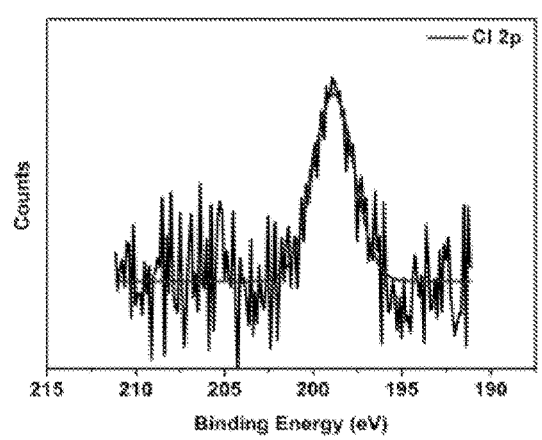

FIG. 8 depicts X-ray photoelectron spectroscopy (XPS) of octapod iron oxide nanoparticles, in accordance with an embodiment of the invention. The solid line represents a fitted curve.

Figure 9:
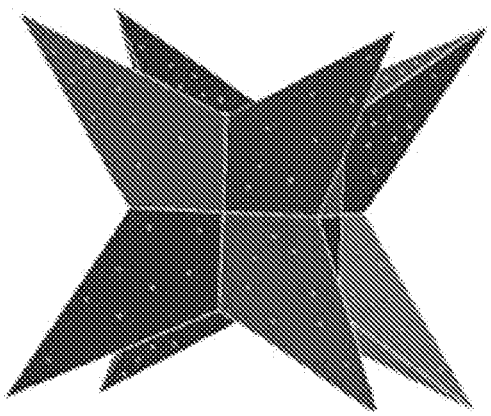

FIG. 9 depicts a model of an octapod iron oxide nanoparticle showing chloride ions, represented as dots, bound to the surface.

Figure 10:
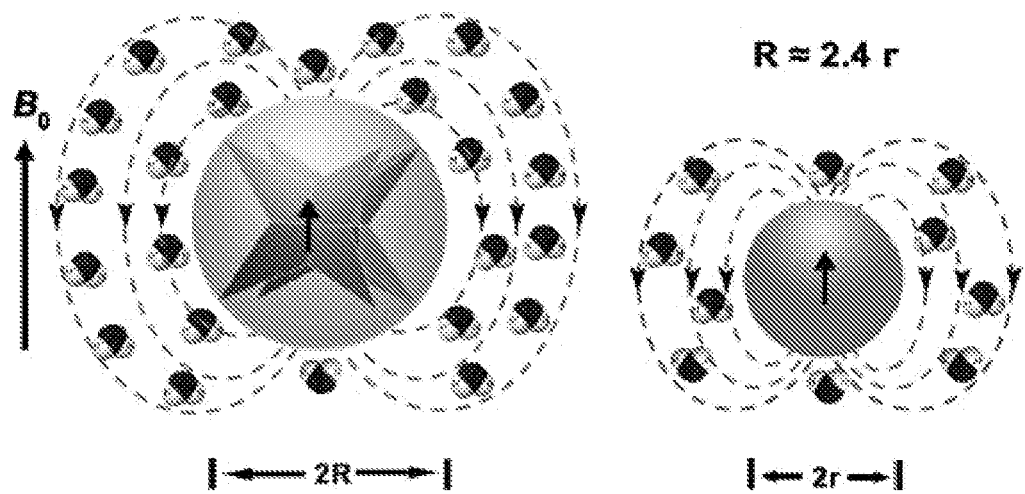

FIG. 10 depicts the effective diameters of octapod iron oxide nanoparticles in comparison with spherical iron oxide particles, in accordance with an embodiment of the invention.

Figure 11:
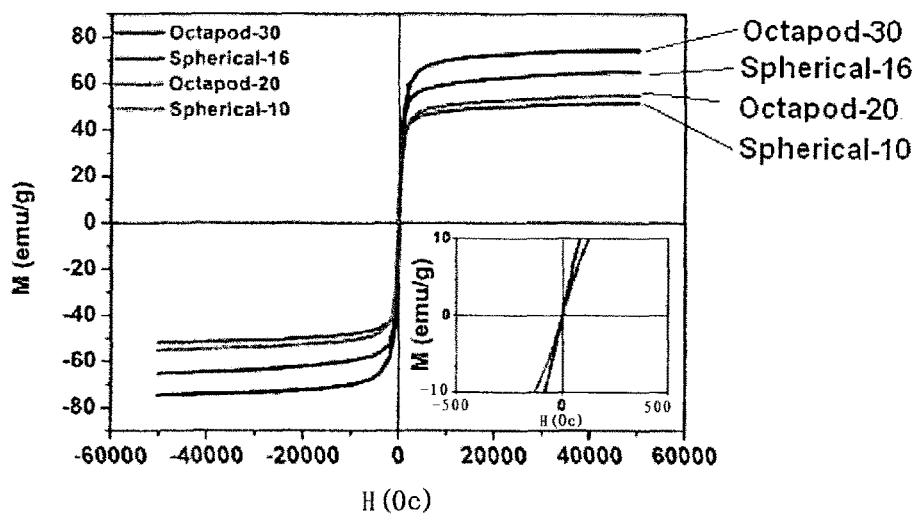

FIG. 11 depicts the M-H (magnetic hysteresis) curves of Octapod-30, Spherical-16, Octapod-20, and Spherical-10 particles, in accordance with an embodiment of the invention.

Figure 12A:
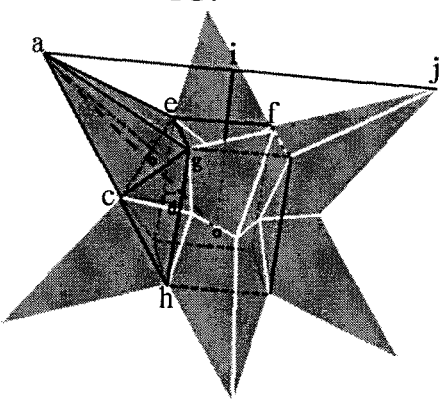
Figure 12B:
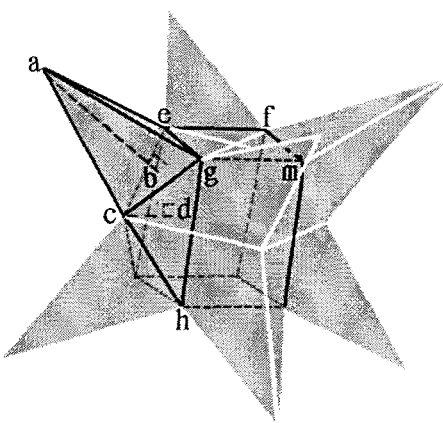

FIGS. 12A and 12B depict the real geometric model and the simplified geometric model of an octapod iron oxide nanoparticle, in accordance with an embodiment of the invention.

Figure 12C:
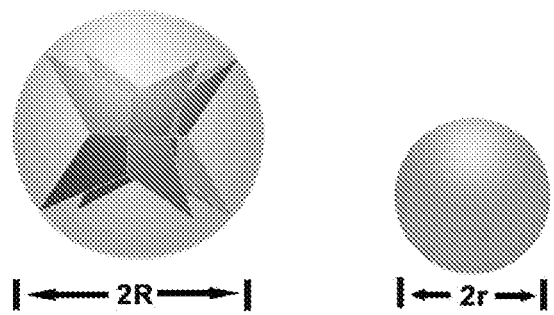

FIG. 12C depicts a schematic of the R (radius) corresponding to the simulated spherical ball which covers the full octapod nanoparticle and the r (radius) corresponding to the spherical nanoparticle with equal geometric volume to the octapod nanoparticle.

Figure 13:
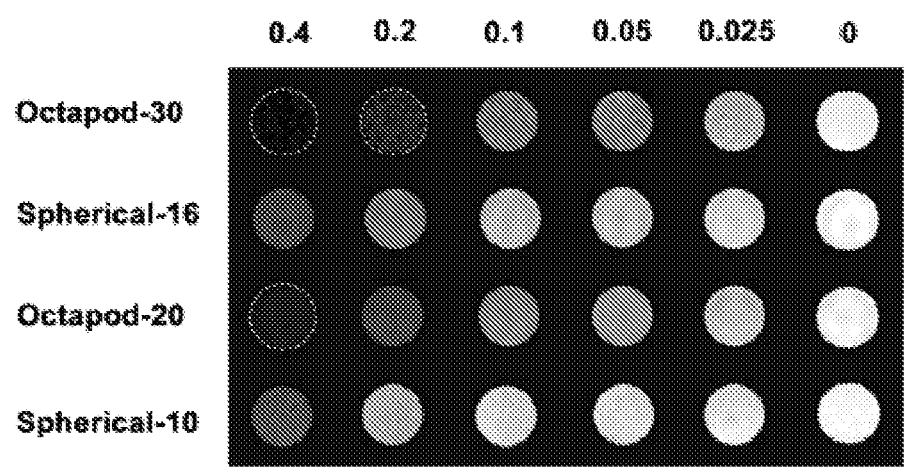

FIG. 13 depicts the $T_2$-weighted phantom images of Octapod-30, Spherical-16, Octapod-20, and Spherical-10 particles as a function of iron concentration, in accordance with an embodiment of the invention.

Figure 14:
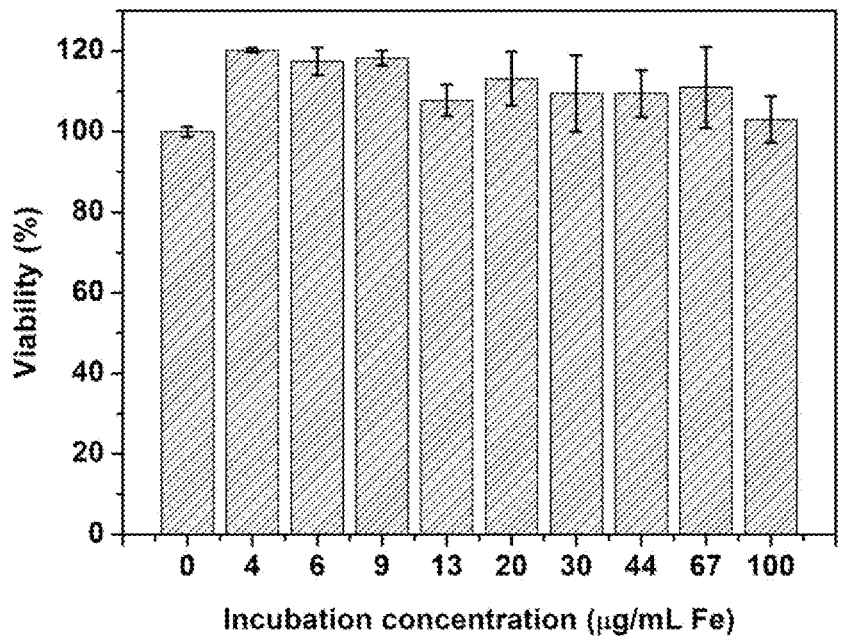

FIG. 14 depicts cell viability data of octapod iron oxide nanoparticles as a function of concentration in an MTT assay for cytotoxicity, in accordance with an embodiment of the invention.

Figure 15:
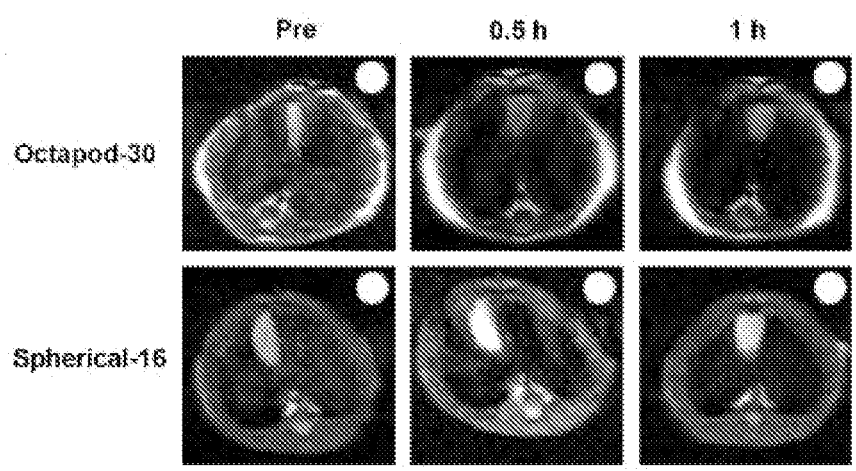

FIG. 15 depicts the $T_2$-weighted MRI images of BALB/c mouse livers at various time points after i.v. injection of Octapod-30 and Spherical-16 at a dosage of 1 mg Fe/kg of body weight of the mice, in accordance with an embodiment of the invention.

Figure 16:
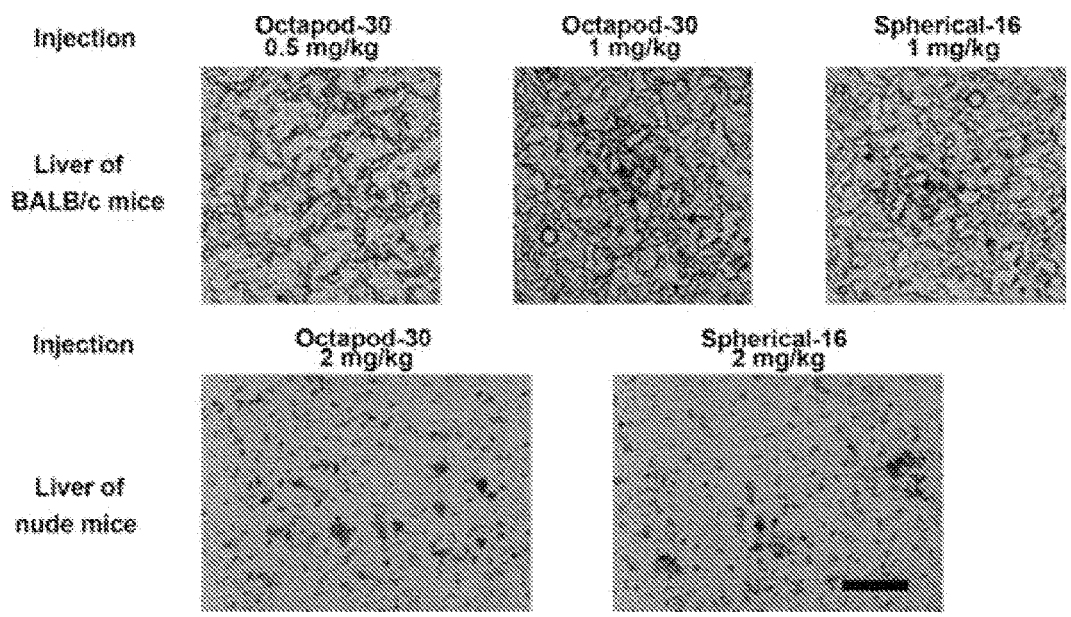

FIG. 16 depicts the Prussian blue staining of BALB/c mouse liver sections at various time points after i.v. injection of Octapod-30 and Spherical-16, in accordance with an embodiment of the invention.

Figure 17:
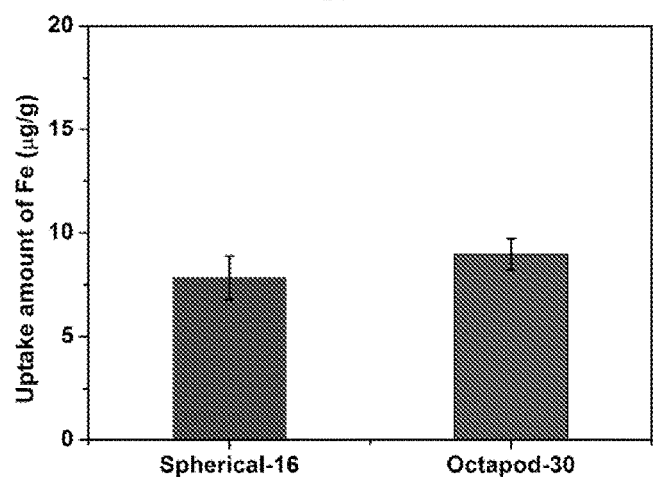

FIG. 17 depicts the liver uptake of iron oxide by BALB/c mouse livers after i.v. injection of Octapod-30 and Spherical-16 as measured by inductively coupled plasma mass spectrometry (ICP-MS), in accordance with an embodiment of the invention.

Figure 18:
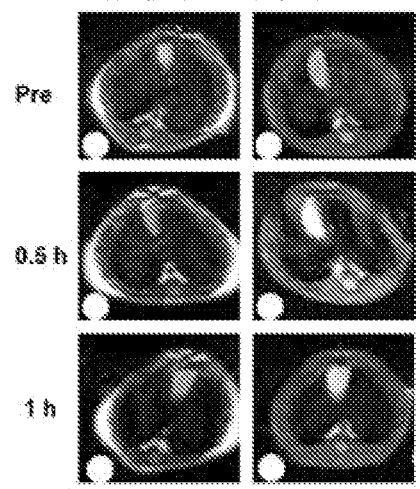

FIG. 18 depicts MRI images of BALB/c mouse livers at various time points after i.v. injection of Octapod-30 and Spherical-16, in accordance with an embodiment of the invention. Octapod-30 and Spherical-16 were administered at a dosage of 0.5 mg Fe/Kg of body weight of the mice and 1 mg Fe/kg of body weight of the mice, respectively.

Figure 19:
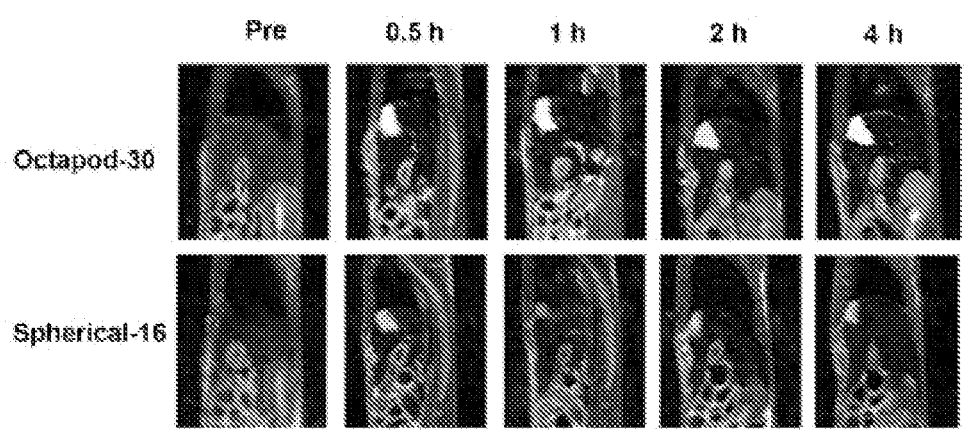

FIG. 19 depicts MRI images of BALB/c mouse livers bearing HepG2 tumors at various time points after i.v. injection of Octapod-30 and Spherical-16, in accordance with an embodiment of the invention.

DETAILED DESCRIPTION OF THE INVENTION

The invention provides nanoparticles comprising octapod iron oxide having eight trigonal bipyramidal arms.

In certain embodiments, the octapod iron oxide comprises $Fe_3O_4$ units. In certain preferred embodiments, the octapod iron oxide comprises magnetite. In certain preferred embodiments, the octapod iron oxide has an inverted spinel crystal structure.

As is known in the art, a spinel is a mineral of the formula: $A^{2+}B_2^{3+}O_4^{2-}$. Magnetite is a spinel of the formula: $Fe^{2+}Fe_2^{3+}O_4^{2-}$.

In any of the above embodiments, the nanoparticles comprise octapod iron oxide and chloride ions. In certain embodiments, the chloride ions are chelated to Fe(III) ions on a surface of the octapod iron oxide. In certain embodiments, the chloride ions are chelated to Fe(III) ions exposed on [311] facets on a surface of the octapod iron oxide.

In any of the above embodiments, the octapod iron oxide comprises a concave polyhedral geometry bounded by [311] high-index facets and having 14 facets and 24 edges. In certain of the above embodiments, the average edge length of the octapod iron oxide is about 15 nm to about 40 nm, for example, about 15 nm, about 20 nm, about 25 nm, 30 nm, 35 nm, or 40 nm.

The invention further provides a method of preparing nanoparticles comprising octapod iron oxide having eight trigonal bipyramidal arms, which method comprises heating a mixture of a ferric carboxylate, a carboxylic acid, a chloride salt, and a solvent. In certain embodiments, the method further comprises a step of isolating the nanoparticles from the mixture. The nanoparticles can be isolated using any suitable technique. For example, the mixture can be cooled to room temperature and the nanoparticles can be precipitated from the reaction mixture by addition of a suitable non-solvent, for example, isopropanol, to the reaction mixture.

The ferric carboxylate is a ferric salt of a carboxylic acid, preferably a long chan fatty acid, for example, a $C_8$-$C_{20}$ carboxylic acid. In certain preferred embodiments, the ferric carboxylate is ferric oleate. In certain preferred embodiments, the carboxylic acid is oleic acid.

In certain preferred embodiments, the chloride salt is an organic or inorganic chloride salt, for example, a metal chloride salt such as sodium chloride or potassium chloride or an organic chloride salt such as a tetraalkylammonium chloride. When the chloride salt is a tetraalkylammonium chloride, the tetraalkylammonium chloride can be any suitable tetraalkylammonium chloride. The tetraalkyl groups can be the same or different, e.g., the alkyl groups can be independently $C_1$-$C_{20}$ alkyl groups. In a preferred embodiment, the tetraalkylammonium chloride is hexadecyl trimethylammonium chloride.

The solvent for running the reaction can be any suitable solvent. In certain embodiments, the non-polar solvent can be selected from alkenes, alkyl ethers, aryl ethers, alkylaryl ethers, amines, and haloaromatics. In certain preferred embodiments, the solvent is a non-polar solvent selected from 1-octadecene, 1-hexadecene, 1-eicosene, phenyl ether, benzyl ether, trioctylamine, octyl ether, and o-dichlorobenzene. In a preferred embodiment, the solvent is 1-octadecene.

Typically, the reaction mixture comprises about 0.1 equivalent or more, about 0.2 equivalent or more, about 0.3 equivalent or more, about 0.4 equivalent or more, or about 0.5 equivalent or more of the chloride salt, relative to 1 equivalent of the ferric carboxylate. Alternatively, or in addition, the reaction mixture comprises about 1 equivalent or less, about 0.9 equivalent or less, about 0.8 equivalent or less, about 0.7 equivalent or less, or about 0.6 equivalent or less. Thus, the reaction mixture can comprise an amount of the chloride salt bounded by any two of the above endpoints. For example, the reaction mixture can comprise about 0.1 to about 1 equivalent, about 0.1 to about 0.9 equivalent, about 0.1 to about 0.8 equivalent, about 0.1 to about 0.7 equivalent, or about 0.2 to about 0.7 equivalent of the chloride salt. The reference to equivalent herein refers to the molar equivalent.

The reaction mixture can be heated for any suitable amount of time. For example, the reaction mixture can be heated for about 0.5 h to about 3 h or longer. The mixture is typically heated to a temperature of about 300° C. to about 350° C., e.g., about 310° C. to about 340° C. or about 320° C. to about 330° C. In embodiments, the average edge length of the octapod iron oxide formed could depend, at least in part, on the length of time the reaction mixture is heated, with the edge length typically increasing with longer reaction mixture heating times.

As used herein, the term "about" when used in conjunction with a numerical value of temperature means that value ±5%, ±4%, ±3%, ±2%, or ±1%. For example, "about 300° C." means 300° C.±15° C., 300° C.±12° C., 300° C.±9° C., 300° C.±6° C., or 300° C.±3° C.

In certain embodiments, the invention provides encapsulated nanoparticles comprising octapod iron oxide having eight trigonal bipyramidal arms, and an encapsulating agent. The encapsulating agent can be any suitable encapsulating agent. Preferably, the encapsulating agent facilitates dispersion of the nanoparticles in a suitable solvent, for example, in water. In preferred embodiments, the encapsulating agent is HDA-$G_2$. HDA-$G_2$ is a dendrimer obtained by condensation of 1-hexadecylamine, methyl acrylate, and ethylene diamine, and its preparation is described in Zhou, Z. J. et al., *Adv. Mater.* 24: 6223-6228 (2012).

In certain embodiments, the encapsulating agent comprises free amine groups. In certain of these embodiments, the encapsulating agent is conjugated to a targeting ligand. Non-limiting examples of suitable targeting ligands include peptides, antibodies, and folic acid. Desirably, the targeting ligand specifically recognizes pathological cells via their surface receptors.

As used herein, the term "targeting ligand" means that a particular molecule binds relatively specifically to molecules present in specific organs or tissues following administration to a subject. In general, selective targeting is characterized, in part, by detecting at least a two-fold greater selective binding of the molecule to an organ or tissue as compared to a control organ or tissue. In certain embodiments the selective binding is at least three-fold or four-fold greater as compared to a control organ or tissue.

In the case of tumor targeting molecules, such molecules bind to receptors that are selectively over-expressed in particular cancer tissues. By over-expression is meant at least one and one half greater expression in tumor tissue compared to normal tissue. In certain embodiments, expression is at least five times greater in tumor as compared to non-tumor.

In embodiments of the present invention, a targeting ligand is attached to the nanoparticles of the present invention that targets specific tissues and tumors. A "targeting ligand" refers to any material or substance that may promote targeting of tissues and/or receptors in vitro or in vivo with the nanoparticles of the present invention. The targeting moiety may be synthetic, semi-synthetic, or naturally-occurring. The targeting moiety may be a protein, peptide, oligonucleotide, or other organic molecule. The targeting moiety may be an antibody (this term including antibody fragments and single chain antibodies that retain a binding region or hypervariable region).

Materials or substances which may serve as targeting ligands include, but are not limited to, the following: antibodies (and fragments such as Fab, RES system F(ab)'2, Fv, Fc, etc,), epidermal growth factor (EGF), cellular receptors, collagen, gelatin, fibrin-binding protein, fibrin, plasminogen activator, thrombus urokinase inhibitor, invasive cells, somatostatin analogs, lectin (WGA), axons, f-Met-Leu-Phe, neutrophils, selectin active fragments, glycosyl structures, ELAM, GMP 140, leucocyte receptors, "RGD" proteins, integrins, granulocytes IL-2, activated T-cells, CD4 HIV infected cells, cationized albumin, fibroblasts, carnitine acetyl, maleyl proteins, macrophage scavenger receptor, hyaluronic acid, lactosylceramide hepatocytes, Asialofoetuin hepatocytes, Arabinogalactan hepatocytes, galactosylated particles, Kupffer cells, terminal fucose Kupffer cells, mannose Kupffer cells, lactose hepatocytes, dimuramyl-tripeptide Kupffer cells, fucoidin-dextran sulfate Kupffer cells, sulfatides, brain glycosyl-steroids, glycosphyngolipids, other glycosylated structures, hypoxia mediators, infarcted tissues, amphetamines, nervous system barbiturates, nervous system sulfonamides, monoamine oxidase inhibitor substrates, brain chemotactic peptides, inflammation sites, muscarine, and dopamine receptor nervous system substrates.

In some embodiments, the invention provides a method of preparing encapsulated nanoparticles comprising octapod iron oxide having eight trigonal bipyramidal arms, which method comprises providing a mixture comprising the aforesaid nanoparticles and an encapsulating agent, and obtaining the encapsulated nanoparticles. Any suitable encapsulating agent may be used in conjunction with the inventive nanoparticles. Non-limiting examples of suitable encapsulating agents include polymers such as polyethylene glycols, functionalized polyethylene glycols (e.g., polyethylene glycol carboxylic acids), polyvinyl alcohols, functionalized polyvinyl alcohols (e.g., polyvinyl alcohol phosphate), ethoxylated fatty alcohols, phospholipids, dendrimers, and the like. In certain preferred embodiments, the encapsulating agent is HDA-$G_2$. The encapsulated nanoparticles can be prepared using any suitable technique. For example, the nanoparticles and the encapsulating agent can be combined in the presence of a solvent, for example, chloroform. After a period of time, the encapsulated nanoparticles can be isolated using any suitable technique. For example, the solvent can be evaporated to provide the encapsulated nanoparticles.

In certain embodiments, the invention provides a method of imaging a tissue in a mammal, comprising administering to the mammal the aforesaid nanoparticles or the aforesaid encapsulated nanoparticles, and obtaining a magnetic resonance image of the tissue. The tissue can be any suitable tissue. The tissue can be any suitable tissue. In certain embodiments, the tissue may be associated with a cancer selected from adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor. In certain embodiments, the tissue is liver tissue. In certain preferred embodiments, the tissue is a liver cancer tissue.

The invention further provides a contrast agent for use in magnetic resonance imaging comprising the aforesaid nanoparticles or the aforesaid encapsulated nanoparticles. In preferred embodiments, the contrast agent is a $T_2$ contrast agent.

The contrast agent of the present invention may be used as a contrast agent for MRI (magnetic resonance imaging), X-ray CT (computed tomography), ultrasound imaging, and scintigraphy. It is particularly suitably used as a contrast agent for MRI. The contrast agent can be administered either parenterally or orally. When the contrast agent is parenterally administered, the contrast agent may further contain known additives such as solvents, suspending agents, etc., used for the production of injection products. Examples of the additives include water, propylene glycol, polyethylene glycol, benzyl alcohol, ethyl oleate, lecithin, etc. These additives may be used alone, or in a combination of two or more. Further, when the contrast agent is orally administered, the contrast agent is administered alone or with a pharmaceutically acceptable carrier. Specifically, the contrast agent is orally administered in the forms of, for example, granules, fine granules, powders, tablets, hard syrup, soft capsules, syrups, emulsions, suspensions, liposomes, solutions, etc. An excipient may be used when forming the granules, fine granules, powders, and tablets. Examples of the excipient include lactose, sucrose, starch, talc, cellulose, dextrin, kaolin, calcium carbonate, etc. These excipients may be used alone, or in a combination of two or more. A generally used inactive diluent may be used when forming the emulsions, syrups, suspensions, and solutions. Examples of the diluent include vegetable oil and the like. The contrast agent may further contain known additives. Examples of the additives include humectants, suspension auxiliary agents, sweeteners, fragrances, colorants, preservatives, etc. These additives may be used alone, or in a combination of two or more. Further, the contrast agent formed in the emulsion or the like may be placed in a capsule made of an absorbable substance, like gelatin. The dosage of administration of the contrast agent of the present invention is not particularly limited: it is 0.1 mg to 10 g, preferably 1 mg to 5 g, per adult in one diagnosis.

Chemistry

Figure 1A:
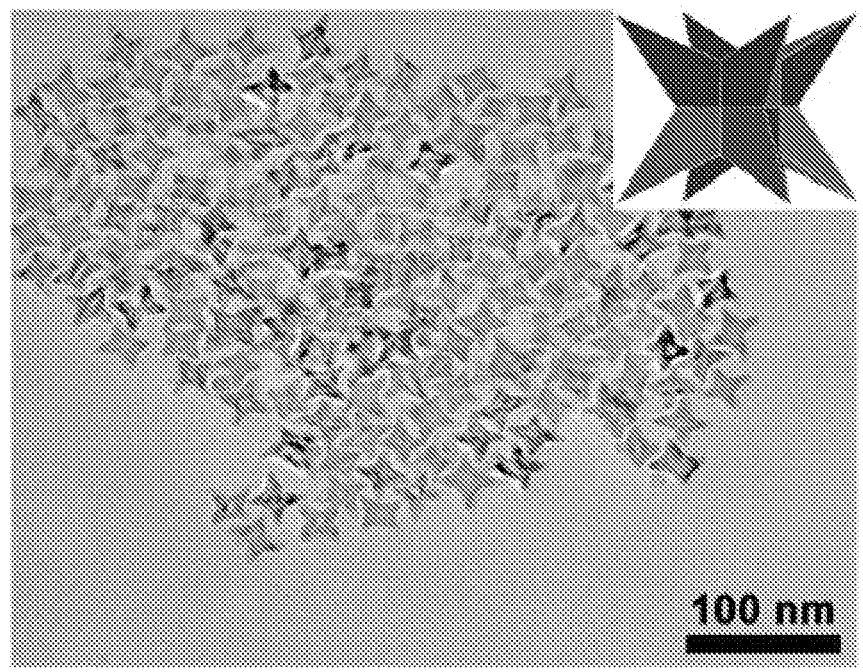
FIGS. 1A and 1B depict transmission electron microscopy (TEM) images of octapod iron oxide nanoparticles at different magnifications in accordance with an embodiment of the invention. The inset in FIG. 1A depicts a proposed concave polyhedral model of the iron oxide nanostructure.
Figure 1B:
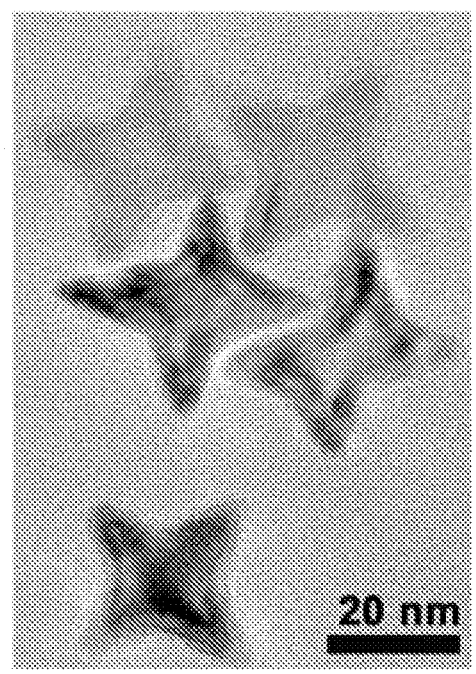
Figure 1C:
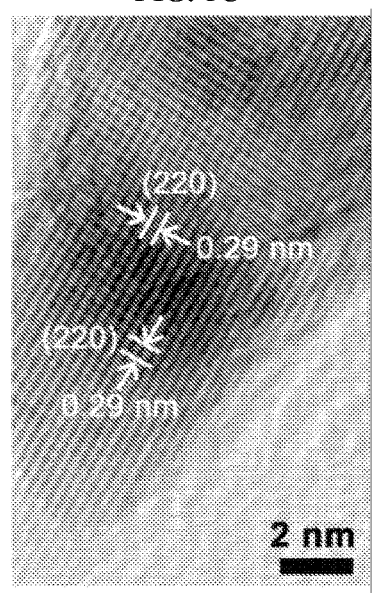
FIG. 1C depicts a high resolution TEM image of octapod iron oxide nanoparticles in accordance with an embodiment of the invention. The uniform lattice fringes across the nanoparticles correspond to Fe$_3$O$_4$ (220).
Figure 1D:
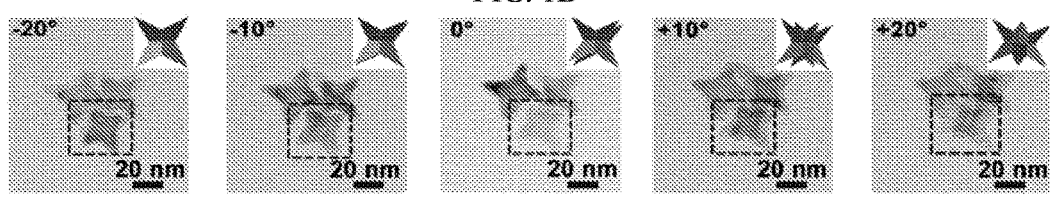
FIG. 1D depicts TEM images of octapod iron oxide nanoparticles at various angles of tilting relative to the electron beam in accordance with an embodiment of the invention. The insets represent a model of the iron oxide nanostructure at the various tilting angles.
Figure 2:
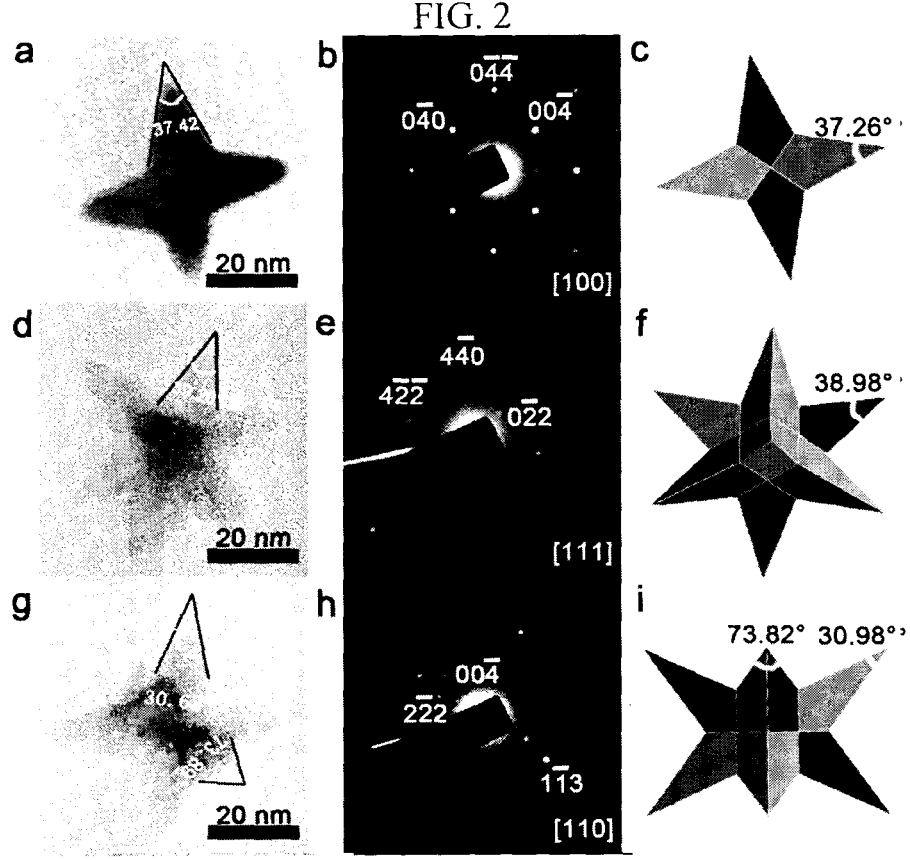
FIG. 2 depicts high resolution TEM images (a, d, g), selected-area electron diffraction (SEAD) images (b, e, h), and geometric models of individual octapod iron oxide nanoparticles oriented along the [100], [111], and [110] directions, respectively, in accordance with an embodiment of the invention.
Figure 3:
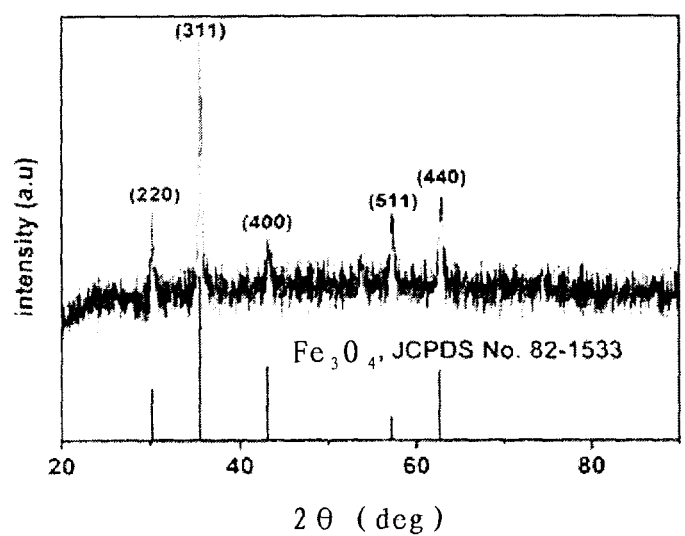
FIG. 3 depicts the X-ray diffraction (XRD) pattern of octapod iron oxide nanoparticles. in accordance with an embodiment of the invention.

The octapod iron oxide nanoparticles were prepared via decomposition of iron oleate in the presence of sodium chloride (NaCl). In an embodiment, the iron oleate was decomposed at 320° C. for 2 h in 1-octadecene containing oleic acid as the surfactant and NaCl as the capping agent. Transmission electron microscopy (TEM) images (FIGS. 1A and 1B) showed that the product obtained consists of uniform four-armed star-like iron oxide particles with high yield (>95%). The average edge length between two nearby armed points is about 30 nm. Uniform lattice fringes were observed across the entire nanoparticles with spacing corresponding to $Fe_3O_4$ (220) in high-resolution TEM (HR-TEM) images (FIG. 1C). After carefully surveying these unique nanoparticles, some shadows were found which likely belong to the four arms of star-like particles, indicating the possible presence of concave feature in the particles. To better visualize the three-dimensional structure of the nanoparticles, the sample was tilted away from the direction perpendicular to the electron beam. Along with the tilting, the nanoparticles changed from four-armed star-like to elongated six-armed stars (FIG. 1D), which fits to the feature of octapod nanoparticles owning eight trigonal pyramidal arms. On the basis of these observations, a concave polyhedral model of this unique iron oxide nanostructure is being proposed (FIG. 1A, inset). To confirm this proposed structure, an individual octapod nanoparticle was characterized by HRTEM and relevant selected-area electron diffraction (SEAD) measurements. Both the outlines and angles between the edges of individual nanoparticle are consistent with the geometric models of concave bounded by [311] high-index facets (FIG. 2). The X-ray powder diffraction (XRD) pattern of octapod nanoparticles matched well with magnetite $Fe_3O_4$ reference values (JCPDS No. 82-1533) without any iron phase, suggesting the octapod iron oxide nanoparticles are pure magnetite with inverse spinel crystal structure (FIG. 3). The XRD pattern showed peaks at 2θ values of about 31, 36, 43, 57, and 63 degrees.

In accordance with an embodiment of the invention, a chloride salt, e.g., NaCl may be essential in the synthesis of octapod iron oxide nanoparticles. The uniform octapod iron oxide nanoparticles were obtained by supplying a certain amount of NaCl (0.17 mmol to 0.86 mmol iron-oleate) to a 10 mL of reaction solution. When the amount of NaCl was reduced to 0.085 mmol, the yield of octapod iron oxide nanoparticles was significantly reduced. There were very few octapod iron oxide nanoparticles when the amount of NaCl was further decreased to 0.034 mmol (FIG. 4). These results suggest that NaCl may play an important role in the formation of octapod iron oxide nanoparticles. To understand the effects of chloride anions and sodium cations in the formation of octapod iron oxide nanoparticles, a number of control experiments were conducted. When using NaOH and Na-oleate instead of NaCl, the products were mainly the mixture of spherical and cubic iron oxide nanoparticles. Further, the octapod structure was not obtained when NaF or KBr were employed instead of NaCl (FIG. 5), indicating that the chloride ions are more critical in the formation of octapod iron oxide nanoparticles than sodium ions. Furthermore, hexadecyl trimethyl ammonium chloride (CTAC), KCl, hexadecyl trimethyl ammonium bromide (CTAB), and KBr were used instead of NaCl to investigate the structures of final products (FIG. 6). Similar octapod products were obtained by adding CTAC or KCl, while no desired octapod structures were obtained in the presence of CTAB or KBr. These results further confirm that the chloride ions are the key inducer of the formation of octapod iron oxide nanoparticles.

It was also possible to control the sizes of octapod nanoparticles by varying the reaction time in the presence of NaCl. The octapod nanoparticles with average edge lengths of 14, 20, 30, and 36 nm were formed by reaction for 0.5, 1, 2, and 2.5 h, respectively (FIG. 7), suggesting that the chloride ions may affect the formation of octapod nanoparticles throughout the particle growth process. One possible mechanism of forming octapod iron oxide nanoparticles was that the chloride ions were selectively bound to iron ions exposed on the high-index facets (probably [311]) of iron oxide during the particle growth. Such a chloride ion-assisted formation mechanism is supported by the observed presence of a trace amount of chloride on the octapod iron oxide nanoparticles using energy-dispersive X-ray spectroscopy (EDS) and X-ray photoelectron spectroscopy (XPS) shown in FIG. 8). FIG. 9 depicts a model showing the presence of chloride ions on the surface of the nanoparticles.

Structure and property of octapod iron oxide nanoparticles. Without wishing to be bound by any theory or mechanism, it is believed that the sophisticated morphology of the nanostructures of embodiments of the invention may alter the effective radii of particle cores. According to the quantum mechanical outer sphere theory, a spherical ball covering the full octapod iron oxide nanoparticle was simulated as a model to represent the objective existence of octapod nanoparticles under an external magnetic field $B_0$ (FIG. 10). Thus, the diameter of the model shows the effective diameters of octapod iron oxide nanoparticles. It was found that the effective radii of octapod iron oxide nanoparticles were approximately 2.4 times as large as that of spherical nanoparticles having the same geometric core volumes, demonstrating that the octapod morphology can significantly increase the effective radii of nanoparticles and indicating that octapod iron oxide nanoparticles may possess much higher $T_2$ relaxivity than the spherical nanoparticles with similar geometric volumes. To investigate the MRI contrast ability of octapod and spherical iron oxide nanoparticles with the same geometric volumes, the octapod iron oxide nanoparticles with average edge lengths of 30 nm (denoted as Octapod-30) and 20 nm (denoted as Octapod-20) were chosen as two representative examples. Accordingly, spherical nanoparticles with mean diameters of 16 nm (denoted as Spherical-16) and 10 nm (denoted as Spherical-10) were used for comparison because of the similarity in volume (i.e., Octapod-30 to Spherical-16 and Octapod-20 to Spherical-10). The magnetic properties of octapod and spherical iron oxide nanoparticles were then tested by a superconducting quantum interference device (SQUID). Octapod-30, Octapod-20, Spherical-16, and Spherical-10 all showed a smooth M-H curve with no hysteresis at ambient temperature (FIG. 11). The blocking temperature of Octapod-30 and Octapod-20 were 290 K and 240 K, respectively, which further confirmed that Octapod-30 and Octapod-20 exhibited superparamagnetic behaviors at room temperature, enabling these nanoparticles for many biomedical applications (e.g., biological separation and MRI contrast enhancement). The $M_s$ values of Octapod-30, Octapod-20, Spherical-16, and Spherical-10 were approximately 71, 51, 67, and 55 emu/g, respectively. The slightly higher $M_s$ value of Octapod-30 than that of Spherical-16 may be due to the reduced spin canting effect in octapod morphology compared to spherical particle. Despite being of similar $M_s$ values, the shape anisotropy in these spiked concave magnetite nanostructures and the significantly increased effective radii of the magnetic cores may be responsible for the distinctly high $T_2$ relaxivities.

A method of calculation of the volume of the octapod nanoparticles is as follows. FIG. 12A depicts the real geometric model, and FIG. 12B depicts the simplified geometric model.

As shown in the simplified geometric model (Scheme S2), the octapod model is composed of 8 tetrahedrons, 4 pyramids, and 1 cube. For simplicity, it was specified that $L_{ef}=\alpha$, $L_{ae}=\beta$, $L_{gh}=\gamma$, $L_{aj}=\delta$, and $L_{io}=\epsilon$. By calculating from the model, it was obtained that $\beta=\sqrt{3}\alpha$, $\gamma=\sqrt{2}\alpha$, $\delta=4\alpha$, and $\epsilon=\sqrt{2}\alpha$.

For the tetrahedron, $$L_{ae} = L_{ag} = L_{ac} = L_{ce} = \alpha$$

and $$L_{ae} = \beta \cdot h_{tet} = L_{ab} = \sqrt{\beta^2 - \left(2/3\left(\sqrt{\alpha^2 - 1/4\alpha^2}\right)\right)^2},$$

$$V_{tet} = 1/3 \times \sqrt{3}/2\alpha \times \alpha \times 1/2 \times h_{tet} = \sqrt{2}/6\alpha^3$$

For the pyramid, $$L_{gh} = c = \sqrt{2}\,\alpha,$$

$$L_{ge} = L_{gc} = L_{ec} = L_{hc} = \alpha \cdot h_{pyr} = \sqrt{\alpha^2 - \left(1/2\left(\sqrt{\gamma^2 + \alpha^2}\right)\right)^2},$$

$$V_{pyr} = 1/3 \times \alpha \times \gamma \times h_{pyr} = \sqrt{2}/6\alpha^3$$

For the cube, $L_{gh}=\sqrt{2}\alpha$, $L_{eg}=L_{ef}=\alpha$. $V_{cub}=\sqrt{2}\alpha \times \alpha \times \alpha = \sqrt{2}\alpha^3$ So $V_{octapod}=8V_{tet}+4V_{pyr}+V_{cub}=\sqrt{2}/6\alpha^3 \times 8+2\sqrt{2}/3\alpha^3 \times 4+\sqrt{2}\alpha^3$, $V_{spherical}=4/3\pi r^3$. When the geometric volumes of octapod particle and spherical particle are the same, $\sqrt{2}/6\alpha^3 \times 8+\sqrt{2}/6\alpha^3 \times 4+\sqrt{2}\alpha^3=4/3\pi r^3$, $r\approx 1.01\alpha$. The areas of octapod and sphere under the same geometric volumes were then compared. $S_{octapod}=24S_{aeg}+6S_{egfm}=\sqrt{11}/2\alpha^2 \times 24+8\alpha^2=12\sqrt{11}\alpha^2+8\alpha^2$. For the sphere, $S_{spherical}=4\pi r^2$ ($r=1.01\alpha$). So $S_{octapod}\approx 3.73 \times S_{spherical}$, means that the surface-to-volume (S/V) ratio of octapod nanoparticle is 3.73 times as high as that of spherical nanoparticle. For the octapod nanoparticle, $$R = \sqrt{\left(\frac{\delta}{2}\right)^2 + g^2} = \sqrt{6}\,\alpha \approx 2.45\alpha,$$

which means $R\approx 2.42r$ under the same geometric volumes (Scheme S3). In the present case, the efficient diameters (2R) of Octapod-30 and Octapod-20 are 40±2 and 26±1 nm, respectively. So the spherical iron oxide nanoparticles with diameters (2r) of about 16 nm and 10 nm were chosen accordingly as control samples for comparison.

FIG. 12C depicts a schematic of the R corresponding to the simulated spherical ball which covers the full octapod nanoparticle and the r corresponding to the spherical nanoparticle with equal geometric volume to the octapod nanoparticle.

As used herein, the term "particle size" refers to the diameter of a sphere that fully encloses a particle.

Because the as-prepared nanoparticles were hydrophobic, the nanoparticles were transferred to aqueous media using the conjugates of dendritic molecules and 1-hexadecylamine (denoted as HDA-$G_2$) by hydrophobic-hydrophobic interaction (Zhou et al., supra). The encapsulated nanoparticles showed excellent colloidal stability in aqueous solution. No aggregation or morphology alteration was observed after storage for more than one month. The hydrodynamic diameters (HDs) of all the samples were measured by dynamic light scattering (DLS). The HDs of Spherical-10, Spherical-16, Octapod-20, and Octapod-30 were 22±2, 30±3, 49±5, and 58±2 nm, respectively, suggesting that the iron oxide nanoparticles were monodispersed in water without any significant clustering and aggregation. Moreover, in these encapsulated nanoparticles, there are a large number of free amine groups available on the surface of the water-dispersible octapod nanoparticles, allowing for further modification and functionalization. It is of note that the HD of Octapod-30 is about twice as much as that of Spherical-16, which is consistent with the proposed model (FIG. 10). In addition, the physical surface-to-volume ratio of Octapod-30 in aqueous medium is larger than that of the simulated spherical model because of the unique octapod structure. Accordingly, it is expected that the effective surface area of Octapod-30 for diffusion of water molecules may be more than 4 times greater than that of Spherical-16.

Transverse relaxivity of octapod iron oxide nanoparticles. The transverse relaxivity ($r_2$) values of the above four samples were tested on a 7 T MR scanner. With the increase of Fe concentrations, the signal intensity of $T_2$-weighted phantom images decreased as expected (FIG. 13), indicating that all the samples have the potential to generate MRI contrast enhancement on $T_2$-weighted sequences. Notably, the octapod iron oxide nanoparticles exhibited stronger $T_2$ contrast effects than spherical iron oxide nanoparticles, suggesting that the octapod iron oxide nanoparticles may serve as highly sensitive $T_2$ contrast agents. The $r_2$ values of Octapod-30, Octapod-20, Spherical-16, and Spherical-10 were about 679.25±30, 209.03±15, 125.86±9, and 59.91±6 $mM^{-1} S^{-1}$, respectively. Due to the increased effective radii of octapod iron oxide cores, the $r_2$ value of Octapod-30 was approximately 5.4 times larger than that of Spherical-16. Meanwhile, Octapod-20 has a higher $r_2$ value than Spherical-10 (about 3.5 times) as well. It should be mentioned that the $M_s$ values and geometric volumes of both octapod iron oxide nanoparticles were very close to the corresponding spherical iron oxide nanoparticles (i.e., Octapod-30 to Spherical-16 and Octapod-20 to Spherical-10). These results demonstrate that structurally increasing the effective radii of iron oxide through morphology control is an attractive alternative to existing strategies such as metal doping and particle clustering to increase the $T_2$ relaxivity of iron oxide nanoparticles.

Liver MR imaging using octapod iron oxide nanoparticles. Before carrying out the animal study, the cytotoxicity of water-dispersible octapod iron oxide nanoparticles were first tested using HepG2 cell line as a model. The 3-(4,5-dimethylthiazol-2-yl)-2,5-diphenyltetrazolium bromide (MTT) assay indicated that the octapod iron oxide nanoparticles have no appreciable cytotoxicity for 24 h even at concentration up to 100 μg Fe/mL, suggesting that the octapod iron oxide nanoparticles are biocompatible (FIG. 14). To verify that octapod iron oxide nanoparticles display better contrast effects than traditional spherical iron oxide nanoparticles in vivo, Octapod-30 and Spherical-16 were chosen as representative samples and conducted $T_2$-weighted MRI of liver using BALB/c mouse as a model. After intravenous injection of Octapod-30 and Spherical-16 samples at a dose of 1 mg Fe/kg of mouse body weight, significant signal attenuation was indeed observed in the liver region for both nanoparticles (FIG. 15) at 0.5 h post-injection (p.i.). To quantify the contrast, the liver was identified as the region of interest (ROI) and the signal-to-noise ratio (SNR) and $SNR_{post}/SNR_{pre}$ value was calculated for each animal and set forth in the Table below.

TABLE

|  | Octopod-30 (1 mg/kg) | Spherical-16 (1 mg/kg) | Octopod-30 (0.5 mg/kg) |
|---|---|---|---|
| $SNR_{pre}$ (%) | 100 | 100 | 100 |
| $SNR_{0.5 h}$ (%) | 36.1 ± 3.2 | 60.2 ± 1.5 | 60.1 ± 2.5 |
| $\Delta SNR_{0.5 h}$ (%) | 63.9 ± 3.2 | 39.8 ± 1.5 | 39.9 ± 2.5 |
| $SNR_{1 h}$ (%) | 32.7 ± 1.3 | 46.5 ± 1.6 | 43.8 ± 1.9 |
| $\Delta SNR_{1 h}$ (%) | 67.3 ± 1.3 | 53.5 ± 1.6 | 56.2 ± 1.9 |

Octapod-30 exhibited much higher contrast (63.9±3.2 and 67.3±1.3% at 0.5 and 1 h p.i., respectively) than Spherical-16 (39.8±1.5 and 53.5±1.6% at 0.5 and 1 h p.i., respectively), suggesting that Octapod-30 with higher $r_2$ value is more sensitive than Spherical-16 in $T_2$ imaging of liver in vivo. Prussian blue staining detected blue spots throughout the liver sections after administration of Octapod-30 and Spherical-16 (FIG. 16), confirming that the signal attenuation in the liver was caused by iron oxide nanoparticle accumulation. The inductively coupled plasma mass spectrometry (ICP-MS) analysis (FIG. 17) indicates that the liver uptake of Octapod-30 and Spherical-16 is in a comparable manner, demonstrating that the much better contrast is due to the higher $r_2$ value of Octapod-30. In MR imaging, lower dose of contrast agents may imply lower cost and less side effect, which pledges greater prospects in clinical diagnosis. The higher contrast of Octapod-30 suggested conducting liver MR imaging at a lower dose. By reducing the injection dose of Octapod-30 to 0.5 mg Fe/kg, the contrast (39.9±2.5% at 0.5 h and 56.2±1.9% at 1 h) was still slightly higher than that of Spherical-16 at 1 mg/kg doses (FIG. 18).

Detection of liver cancer by MRI using octapod iron oxide nanoparticles. To further evaluate the ability of Octapod-30 for liver cancer imaging, a $T_2$-weighted MRI was conducted on an orthotopic HepG2 tumor model. The orthotopic liver tumor model was established by inoculation of small subcutaneous HepG2 tumor fragments into the liver of nude mice. When the hepatic carcinoma reached 3-5 mm in diameter, Octapod-30 and Spherical-16 were intravenously injected into the nude mice (2 mg Fe/kg) and the animals were scanned on a 7 T microMRI scanner. Since hepatic tumors contain much less active Kupffer cells and macrophages, they do not accumulate iron oxide nanoparticles as efficiently as normal liver tissues do. Thus, the hepatic tumors would show pseudo-positive contrast as compared to normal liver tissues. Both particles caused obvious contrast enhancement in the tumor sites after intravenous administration (FIG. 19). However, the injection of Octapod-30 resulted in higher MR contrast in the tumor site than Spherical-16, leading to easier differentiation between the liver lesions and normal liver tissues in the MR images. The tumor-to-liver contrast increased over time and was as high as 136.9±8.5 and 64.5±2.7% at 4 h p.i. for Octapod-30 and Spherical-16, respectively, indicating that Octapod-30 exhibited much higher signal changes for liver tumor imaging and detection limit than Spherical-16. The use of Octapod-30 with ultrahigh $T_2$ relaxivity as contrast agent may thus significantly improve the sensitivity of $T_2$ imaging, which should be extremely important for accurate detection and early diagnosis of cancer.

General Procedures $FeCl_3$, NaCl, KCl, KBr, NaF, hexane, sodium oleate, isopropanol, and ethanol were purchased from Sinopharm Chemnica Reagent Co. Ltd (Shanghai, China. 1-Octadecene (90%), oleic acid (90%), hexadecyl trimethyl ammonium chloride, and hexadecyl trimethyl ammonium bromide were purchased from Alfa Aesar (Ward Hill, Mass.). All reagents were used as received without further purification.

Measurement of MR relaxivity of iron oxide nanoparticles. To measure the $T_2$ relaxivity, Octapod-30, Octapod-20, Spherical-16, and Spherical-10 with different iron concentrations were dispersed in 1% agarose solution. The samples were scanned using a multi-echo $T_2$-weighted fast spin echo imaging sequence (TR/TE=2000/20, 40, 60, 80, 100 ms, slice thickness=2 mm) on a 7 T MRI scanner (Varian 7 T micro MRI System).

Cell culture. The HepG2 cells were purchased from Cell Bank of Chinese Academy of Sciences (Shanghai, China) and cultured in Dulbecco's Modified Eagle's Medium (DMEM medium) supplemented with 10% fetal bovine serum (FBS, Hyclone) and antibiotics (100 mg/mL streptomycin and 100 U/mL penicillin) All cells maintained in a humidified atmosphere of 5% $CO_2$ at 37° C.

In vitro cytotoxicity evaluation. The HepG2 cells ($1 \times 10^4$) were seeded in 96-well plates and incubated for 12 h in DMEM (containing 10% FBS). After washed cells twice with PBS, fresh medium containing octapod iron oxide nanoparticles was added at different concentrations (the equivalent Fe concentrations were 100, 67, 44, 30, 20, 13, 9, 6, 4, and 0 µg Fe/mL) and the cells incubated for 24 h. Each experiment in the same concentration was performed in five wells. The growth medium was replaced with DMEM containing 0.5 mg/mL of 3-(4,5-dimethylthiazol-2-yl)-2,5-diphenyltetrazolium bromide (MTT) and the cells incubated for another 4 h. The culture medium was discarded and 100 µL of DMSO was added to dissolve the precipitates and the resulting solution was measured for absorbance at 492 nm using a MultiSkan FC microplate reader (Thermo Scientific).

In vivo liver MR imaging Animal experiments were executed according to the protocol approved by Institutional Animal Care and Use Committee of Xiamen University. The in vivo MR imaging of liver was performed by using the BALB/c mouse as a model. After intravenous injection of iron oxide nanoparticles at a dose of 1 mg Fe/kg of mouse body weight, the coronal and transverse plane MR images were scanned using an fSEMS sequence (TR/TE=3000/40 ms, 256×256 matrices, averages=1) on a Varian 7 T microMRI scanner. The MR images were obtained at pre-injection, 0.5, and 1 h post-injection (n=3/group). To quantify the signal enhancement, the signal-to-noise ratio (SNR) was calculated by the equation: $SNR_{liver}=SI_{liver}/SD_{noise}$, where SI represents signal intensity and SD represents standard deviation.

In vivo liver tumor MR imaging. The orthotopic liver tumor model was established by inoculation of small subcutaneous HepG2 tumor fragments into the liver of nude mice. When the tumor reached 3-5 mm in diameter, mice were intravenously injected with Octapod-30 and Spherical-16 at a dose of 2 mg Fe/kg. The coronal and transverse plane MR images were acquired using an fSEMS sequence (TR/TE=3000/40 ms, 256×256 matrices, Averages=1) on a 7 T MRI scanner. The MR images were sequentially obtained at 0, 0.5, 1, 2, and 4 h post-injection (n=3/group). To qualify the efficacy of contrast enhancement, the contrast-to-noise ratio (CNR) was introduced, which was given by $CNR=(SNR_{tumor}-SNR_{liver})/SNR_{tumor}$.

Prussian blue staining After MR imaging, the mice were sacrificed and the livers of mice were kept in the optimal-cutting-temperature (O.C.T) compound and stored at −80° C. When the mixture was frozen, the samples were cut into 10 µm thick slices and fixed with ice-cold acetone for 5 min immediately. After drying at room temperature for 5 min, the slide was put into the staining solution (20% hydrochloric acid and 10% potassium ferrocyanide solution mixture, 1:1 volume ratio) for 30 min, and counterstained with eosin for 5 min. Then, 90%, 95%, and pure water were used to clean the slides 3 times.

The following examples further illustrate the invention but, of course, should not be construed as in any way limiting its scope.

Example 1

This example demonstrates a synthesis of iron oleate.

4.56 g of sodium-oleate (15 mmol) and 0.81 g of $FeCl_3$ (5 mmol) were dissolved in a mixture of 20 mL of distilled water and 10 mL of ethanol. The resulting solution was heated to 70° C. and kept at that temperature for 4 h under argon atmosphere. When the reaction was completed, hexane was added, and the hexane layer was washed three times with distilled water in a separatory funnel. After hexane was evaporated, the iron-oleate complex was obtained in a waxy solid form.

Example 2

This example demonstrates a synthesis of comparative spherical iron oxide nanoparticles with a size of 16 nm.

The synthesis of spherical iron oxide nanoparticles was carried out by a procedure published elsewhere (Park et al., Nat. Mater. 2004, 3: 891-895. 0.93 g Iron-oleate (1 mmol) synthesized as described in Example 1 and 160 µL oleic acid (0.5 mmol) were dissolved in 15 mL 1-octadecene at room temperature. The mixture was degassed in vacuum for 30 min and backfilled with argon to remove any low volatile impurities and oxygen at room temperature. The reaction solution was then heated to 320° C. with a constant heating rate of 3.3° C. $min^{-1}$, and kept at that temperature for 1 h. The initial reddish-brown color of reaction solution turned brownish-black. The resultant solution was then cooled to room temperature and mixed with 30 mL isopropanol to precipitate the nanoparticles. The nanoparticles were separated by centrifugation and washed 3 times with ethanol. After washing, the nanoparticles were dissolved in hexane for long term storage at 4° C.

Example 3

This example demonstrates a synthesis of comparative synthesis of spherical iron oxide nanoparticles with a size of 25 nm.

0.93 g Iron-oleate (1 mmol) and 160 µL oleic acid (0.5 mmol) were dissolved in 10 mL trioctylamine at room temperature. The mixture was degassed at room temperature in vacuum for 30 min and backfilled with argon to remove any low volatile impurities and oxygen. The reaction solution was heated to 350° C. with a constant heating rate of 3.3° C. $min^{-1}$, and kept at that temperature for 5 h. The initial reddish-brown color of the reaction solution turned into brownish-black. The resulting solution was then cooled to room temperature and mixed with 30 mL ethanol to precipitate the nanoparticles. The nanoparticles were separated by centrifugation and washed 3 times with ethanol. After washing, the nanoparticles were dissolved in hexane for long term storage at 4° C.

Example 4

This example demonstrates a synthesis of octapod iron oxide nanoparticles with an edge length of 30 nm, in accordance with an embodiment of the invention.

Iron oleate (0.8 g, 0.86 mmol), NaCl (10 mg, 0.17 mmol), oleic acid (110 μL, 0.35 mmol), and distilled water (60 μL) were mixed together with 10 mL of 1-octadecene. The resulting solution was degassed in vacuum for 30 min and backfilled with argon to remove any low volatile impurities and oxygen at room temperature. The reaction solution was heated to 320° C. with a constant heating rate of 3.3° C. $min^{-1}$, and kept at the temperature for 2 h. The color of the solution changed from reddish-brown to transparent orange and finally brownish-black. The solution was cooled to room temperature and mixed with 30 mL of isopropanol to precipitate the nanoparticles. The nanoparticles were separated by centrifugation and washed 3 times with ethanol. The resulting product was dissolved in hexane for long-term storage at 4° C.

Example 5

This example demonstrates a synthesis of octapod iron oxide nanoparticles with an edge length of 20 nm, in accordance with an embodiment of the invention.

The synthesis of octapod iron oxide nanoparticles with the edge length of 20 nm was carried out as described in Example 4 except that after heating to 320° C., the solution was kept at that temperature for 1 h. The nanoparticles were separated by centrifugation and washed 3 times with ethanol. The nanoparticles were dissolved in hexane for long term storage at 4° C.

Example 6

This example demonstrates a preparation of water soluble HDA-$G_2$ encapsulated nanoparticles.

Octapod iron oxide nanoparticle complexes with HDA-$G_2$ were obtained by coprecipitation of nanoparticles and HDA-$G_2$. 1 mL of chloroform containing 20 mg of HDA-$G_2$ was added to 1 mL of chloroform containing 10 mg of octapod iron oxide nanoparticles, and the container was left open in a fume hood to evaporate the solvent slowly at room temperature. The residual chloroform was removed completely by pump, and the dry sample was re-dispersed in water by sonication. Further purification of the water-dispersible sample was performed by size exclusion chromatography (PD-10 column, GE Healthcare Life Science). The final aqueous solution was stored at 4° C. for further use.

The invention includes the following aspects or embodiments:

1. Nanoparticles comprising octapod iron oxide having eight trigonal bipyramidal arms.
2. The nanoparticles of aspect 1, wherein the octapod iron oxide comprises $Fe_3O_4$ units.
3. The nanoparticles of aspect 1 or 2, wherein the octapod iron oxide comprises magnetite.
4. The nanoparticles of any one of aspects 1-3, wherein the iron oxide has an inverted spinel crystal structure.
5. The nanoparticles of any one of aspects 1-3, wherein the octapod iron oxide comprises chloride ions.
6. The nanoparticles of aspect 5, wherein the chloride ions are chelated to Fe(III) ions on a surface of the octapod iron oxide.
7. The nanoparticles of aspect 5, wherein the chloride ions are chelated to Fe(III) ions exposed on [311] facets on a surface of the octapod iron oxide.
8. The nanoparticles of any one of aspects 1-7, wherein the octapod iron oxide comprises a concave polyhedral geometry bounded by [311] high-index facets and having 14 facets and 24 edges.
9. The nanoparticles of any one of aspects 1-8, wherein an average edge length of the octapod iron oxide is about 15 nm to about 40 nm.
10. Encapsulated nanoparticles comprising nanoparticles of any one of aspects 1-9 and an encapsulating agent.
11. The encapsulated nanoparticle of aspect 10, wherein the encapsulating agent is HDA-$G_2$.
12. The encapsulated nanoparticle of aspect 10, wherein the encapsulating agent comprises free amine groups.
13. The encapsulated nanoparticle of any one of aspects 10-12, wherein the encapsulating agent is conjugated to a targeting ligand.
14. A method of preparing nanoparticles comprising octapod iron oxide having eight trigonal bipyramidal arms, which method comprises heating a mixture of a ferric carboxylate, a carboxylic acid, a chloride salt, water, and a non-polar solvent, to a temperature above about 300° C.
15. The method of aspect 14, further comprising a step of isolating the nanoparticles from the mixture.
16. The method of aspect 14 or 15, wherein the ferric carboxylate is ferric oleate.
17. The method of any one of aspects 14-16, wherein the carboxylic acid is oleic acid.
18. The method of any one of aspects 14-17, wherein the solvent is a non-polar solvent.
19. The method of aspect 18, wherein the non-polar solvent is selected from alkenes, alkyl ethers, aryl ethers, alkylaryl ethers, amines, and haloaromatics.
20. The method of aspect 19, wherein the solvent is selected from 1-octadecene, 1-hexadecene, 1-eicosene, phenyl ether, benzyl ether, trioctylamine, octyl ether, and o-dichlorobenzene.
21. The method of aspect 20, wherein the solvent is 1-octadecene.
22. The method of any one of aspects 14-21, wherein the chloride salt is an organic or inorganic chloride salt.
23. The method of aspect 21, wherein the chloride salt is selected from sodium chloride, potassium chloride, and tetraalkylammonium chloride.
24. The method of any one of aspects 14-23, wherein the mixture comprises about 0.1 equivalent to about 1 equivalent of the chloride salt, based on an amount of the ferric carboxylate.
25. The method of any one of aspects 14-24, wherein the mixture is heated for about 0.5 h to about 3 h.
26. The method of any one of aspects 14-25, wherein the mixture is heated to a temperature of about 300° C. to about 350° C.
27. A method of preparing encapsulated nanoparticles comprising octapod iron oxide having eight trigonal bipyramidal arms, which method comprises providing a mixture comprising the nanoparticles of aspect 1 and an encapsulating agent, and obtaining the encapsulated nanoparticles.
28. The method of aspect 27, wherein the encapsulating agent is HDA-$G_2$.

29. A method of imaging a tissue in a mammal, comprising administering to the mammal the nanoparticles of any one of aspects 1-9, or the encapsulated nanoparticles of any one of aspects 10-13, and obtaining a magnetic resonance image of the tissue.

30. The method of aspect 29, wherein the tissue is liver tissue.

31. The method of aspect 30, wherein the liver tissue is a liver cancer tissue.

32. A contrast agent for use in magnetic resonance imaging, comprising the octapod iron oxide nanoparticles of any one of aspects 1-9 or the encapsulated nanoparticles of any one of aspects 10-13.

33. The contrast agent of aspect 32, wherein the contrast agent is a $T_2$ contrast agent.

34. Nanoparticles comprising octapod iron oxide having eight trigonal bipyramidal arms as obtained by the method of any one of aspects 14-26.

35. Encapsulated nanoparticles comprising nanoparticles comprising octapod iron oxide having eight trigonal bipyramidal arms as obtained by the method of any one of aspects 14-26, and an encapsulating agent.

36. Encapsulated nanoparticles comprising nanoparticles comprising octapod iron oxide having eight trigonal bipyramidal arms as obtained by the method of aspect 27 or 28.

37. Use of the nanoparticles of any one of aspects 1-9, or the encapsulated nanoparticles of any one of aspects 10-13, in a method of imaging a tissue in a mammal.

38. The use of aspect 37, wherein the tissue is liver tissue.

39. The use of aspect 38, wherein the liver tissue is a liver cancer tissue.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. Isolated nanoparticles comprising octapod iron oxide, wherein the octapod iron oxide consists of magnetite and chloride ions, wherein the iron oxide has a shape characterized by eight trigonal bipyramidal arms, a concave polyhedral geometry bounded by (311) high-index facets, 14 facets in total, and 24 edges, and wherein the chloride ions are chelated to Fe(III) ions exposed on the (311) facets.

2. The nanoparticles of claim 1, wherein the octapod iron oxide has an inverted spinel crystal structure.

3. The nanoparticles of claim 1, wherein an average edge length of the octapod iron oxide is about 15 nm to about 40 nm.

4. Encapsulated nanoparticles comprising nanoparticles of claim 1 and an encapsulating agent.

5. The encapsulated nanoparticle of claim 4, wherein the encapsulating agent is HDA-$G_2$.

6. The encapsulated nanoparticle of claim 4, wherein the encapsulating agent comprises free amine groups.

7. The encapsulated nanoparticle of claim 4, wherein the encapsulating agent is conjugated to a targeting ligand.

8. A method of preparing isolated nanoparticles comprising octapod iron oxide, wherein the octapod iron oxide consists of magnetite and chloride ions, wherein the octapod iron oxide has a shape characterized by eight trigonal bipyramidal arms, a concave polyhedral geometry bounded by (311) high-index facets, 14 facets in total, and 24 edges, and wherein the chloride ions are chelated to Fe(III) ions exposed on (311) facets, which method comprises heating a mixture of a ferric carboxylate, a carboxylic acid, a chloride salt, water, and a non-polar solvent, to a temperature above about 300° C., and then isolating the nanoparticles from the mixture.

9. The method of claim 8, wherein the ferric carboxylate is ferric oleate.

10. A method of preparing encapsulated nanoparticles comprising octapod iron oxide having eight trigonal bipyramidal arms, which method comprises providing a mixture comprising the nanoparticles of claim 1 and an encapsulating agent, and obtaining the encapsulated nanoparticles.

11. Nanoparticles comprising octapod iron oxide having eight trigonal bipyramidal arms as obtained by the method of claim 8.

12. A method of imaging a tissue in a mammal, comprising administering to the mammal the nanoparticles of claim 1, and obtaining a magnetic resonance image of the tissue.

13. The method of claim 12, wherein the tissue is a liver cancer tissue.

14. The nanoparticles of claim 1, wherein the nanoparticles have an edge length of from 20 nm to 30 nm and a transverse relaxivity ($r_2$) value at a magnetic field strength of Tesla of from 209 mM$^{-1}$ S$^{-1}$ to 679 mM$^{-1}$ S$^{-1}$.

* * * * *